(12) United States Patent
Heymans

(10) Patent No.: US 9,260,374 B2
(45) Date of Patent: Feb. 16, 2016

(54) PROCESS FOR THE MANUFACTURE OF α,α-BRANCHED CARBOXYLIC ACID VINYL ESTERS

(75) Inventor: Denis Heymans, Vondelingenplaat (NL)

(73) Assignee: HEXION INC., Columbus, OH (US)

( * ) Notice: Subject to any disclaimer, the term of this patent is extended or adjusted under 35 U.S.C. 154(b) by 0 days.

(21) Appl. No.: 14/007,699

(22) PCT Filed: Apr. 3, 2012

(86) PCT No.: PCT/EP2012/001478
§ 371 (c)(1),
(2), (4) Date: Oct. 10, 2013

(87) PCT Pub. No.: WO2012/136353
PCT Pub. Date: Oct. 11, 2012

(65) Prior Publication Data
US 2014/0303387 A1  Oct. 9, 2014

(30) Foreign Application Priority Data
Apr. 7, 2011 (EP) .................................... 11002898

(51) Int. Cl.
| | | |
|---|---|---|
| C07C 51/00 | (2006.01) | |
| C07C 67/38 | (2006.01) | |
| C08K 5/101 | (2006.01) | |
| C07C 67/04 | (2006.01) | |
| C07C 51/14 | (2006.01) | |
| C08F 220/04 | (2006.01) | |
| C07C 69/533 | (2006.01) | |
| C07C 69/56 | (2006.01) | |

(52) U.S. Cl.
CPC ................. *C07C 67/38* (2013.01); *C07C 51/14* (2013.01); *C07C 67/04* (2013.01); *C07C 69/533* (2013.01); *C07C 69/56* (2013.01); *C08F 220/04* (2013.01); *C08K 5/101* (2013.01)

(58) Field of Classification Search
CPC ........ C07C 67/38; C07C 51/14; C07C 67/04; C07C 69/533; C07C 69/56; C08F 220/04; C08K 5/101
USPC ......................................................... 554/128
See application file for complete search history.

(56) References Cited

FOREIGN PATENT DOCUMENTS

| EP | 1033360 | * | 9/2000 |
|---|---|---|---|
| EP | 1033360 A1 | | 9/2000 |
| JP | 3350709 B2 | | 11/2002 |
| WO | WO 01/56966 A1 | | 8/2001 |
| WO | WO0156966 | * | 8/2001 |

* cited by examiner

*Primary Examiner* — Deborah D Carr

(57) ABSTRACT

The invention relates to a process for the manufacture of α,α-branched carboxylic acids vinyl esters comprising the following steps:
isomerizing and converting an olefin feed with CO and water under Koch reaction conditions to make an acid with a ratio of Non Blocking isomers (NB) versus Blocking isomers (B) of NB/B above 1.5, wherein a blocking isomer has always a tertiary carbon atom in alpha position of the carboxylic acid and in the beta position of the carboxylic acid, whereas a non-blocking isomer has primary carbon atoms in the beta position of the carboxylic acid
converting the resulting acid into a vinyl ester.

7 Claims, No Drawings

PROCESS FOR THE MANUFACTURE OF α,α-BRANCHED CARBOXYLIC ACID VINYL ESTERS

The invention relates to a process for the manufacture of α,α-branched carboxylic acid vinyl esters. More in particular the invention relates to a process for the manufacture of α,α-branched carboxylic acid vinyl esters from olefins by means of a Koch synthesis using carbon monoxide as reagent and an acid catalyst and a subsequent vinylation of the α,α-branched acid.

Processes for the preparation of α,α-branched carboxylic acids from branched olefins by means of a Koch synthesis, using carbon monoxide and water, are known. Thus, Koch, Gilfert and Huiskens developed in 1955 a two-stage operation (medium pressure synthesis where, in the first stage olefins react with an acid catalyst and carbon monoxide in the absence of water, followed by a second stage wherein the complex formed by the olefin, carbon monoxide and the acid catalyst is hydrolyzed. The reaction occurs at temperatures between 50 to 200° C. and pressures up to 100 bar. Generally $H_2SO_4$, $H_3PO_4$, HF or Lewis acids such as $BF_3$ are employed as catalyst. A review of Koch reactions, which review is included herein by reference, may be found in "New Synthesis with Carbon Monoxide", edited by J. Falbe, ISBN 3-540-09674-4, © by Springer-Verlag Berlin Heidelberg 1980. Such technology is also described in U.S. Pat. No. 3,068,256 to Roming, included herein by reference, and in other patent literature.

From EP 1 033 360 a process is known for the synthesis of vinyl esters from butene oligomers, wherein butenes are oligomerized, the butene oligomers are separated from the oligomerized mixture, the butene oligomers are converted to carboxylic acids which are longer by one carbon atom, and the resulting carboxylic acids are converted to the corresponding vinyl esters. The butene oligomers are in particular dibutene, tributene and tetrabutene.

The vinyl esters are well known in the industry as monomer copolymerized with other unsaturated functional olefins that are used in coatings, adhesives and composite applications.

The carboxylic acids obtained by way of the Koch synthesis may be converted to the corresponding vinyl esters. This can be achieved, for example, by reacting the carboxylic acids with acetylene at normal pressure and 200 to 250° C., preferably in the presence of the zinc salt of the acid to be vinylated (for example, according to Encyl. Polym. Sci. Eng. 17, pp. 426-434, incorporated herein by reference). They may also be produced from the corresponding acid by reaction with ethylene and a copper catalyst.

Alternatively, the vinyl esters can be obtained by transesterification of the carboxylic acids with further vinyl esters such as vinyl acetate or vinyl propionate (as described, for example, in: Ullman, 4th Edition, Volume 19, pp. 368 ff., incorporated herein by reference. Industry may start from different sources of olefin oligomers to make the acid. Surprisingly, the inventors have found that the isomer distribution of an olefin oligomer mixture, and more specially the mixture based on a propylene trimer (so called PT3), has an important influence on the throughput of the synthesis of the vinyl ester. This relationship was not disclosed so far. On the other hand, it is obvious that a higher throughput is leading to economical and environmental benefits.

Surprisingly, the inventors have found a way to produce acid composition at a higher throughput in the vinylation step, as compared with the initial isomer composition.

Accordingly, the current invention relates to a process for the manufacture of an α,α-branched carboxylic acid vinyl ester as claimed in claim 1. The invention is of particular relevance when using a propylene oligomer as olefin feed, in particular a PT3 mixture with a high concentration of highly branched isomers. Moreover, the invention is of particular relevance when the branched carboxylic acid produced by the adapted Koch reaction is subsequently converted into a vinyl ester by reaction with acetylene.

The invention is described in more detail hereinafter. The invention is described with respect to propylene oligomers. However, it is to be understood that the improved process may be used with other olefin mixtures with a high content of highly branched isomers as well. Thus, the inventors have found new Koch reaction conditions that allow conversion of commercially available propylene oligomers at improved throughput into a vinyl ester of an α,α-branched carboxylic acid.

The vinyl esters produced accordingly show attractive properties in coating, adhesive or composite applications. They have copolymer Tg (V10/VA: 25/75) of 26.5° C. or lower, wherein V10 represents the vinylester of a C10 acid, and VA represents vinyl acetate.

A propylene oligomer composition is rather complex and variable. For example, the composition of a PT3 may contain olefins with 6, 7, 8, 9, 12 and more carbon atoms. The commercially available PT3 grades generally contain from 90 to 98 weight % of C9. However the isomeric composition within the C9 differs greatly, which has been found to influence the vinylation step.

The current process of the invention comprises the determination of the isomeric composition of the olefin mixture, using KOCH reaction conditions that are adapted to the isomeric composition.

Determination of the isomer composition of e.g. a PT3 stream may be done in various ways. One is by hydrogenating the olefin mixture and identification by gas chromatography. The isomers so identified may be grouped in isomers with one branching alkyl group (such as methyl octane) (BR1), with two branching alkyl groups (such as dimethyl heptane) (BR2) and with three (or more) branching alkyl groups (such as trimethyl hexane) (BR3). Table 1 reports the different isomers identified in PT3 feeds. Identification of the hydrogenated PT3 stream was done to simplify the isomer composition of the alkene content of PT3. In theory 219 C9 alkene isomers are possible and after hydrogenation only 38 C9 alkane isomers are derived there from. So for example the 2,3-dimethylheptane can be produced from 10 different "nonene" isomers by hydrogenation, see Table 1 for the complete overview.

TABLE 1

Nonane isomers in a hydrogenated PT3 stream and identification by gas chromatography

| Code | Name | Number of alkene (1) | Level branching |
|---|---|---|---|
| 901 | n-nonane | 7 | 0 |
| 902 | 2-methyloctane | 11 | 1 |
| 903 | 3-methyloctane | 13 | 1 |
| 904 | 4-methyloctane | 13 | 1 |
| 905 | 2,2-dimethylheptane | 7 | 2 |
| 906 | 2,3-dimethylheptane | 10 | 2 |
| 907 | 2,4-dimethylheptane | 10 | 2 |
| 908 | 2,5-dimethylheptane | 10 | 2 |
| 909 | 2,6-dimethylheptane | 4 | 2 |
| 910 | 3,3-dimethylheptane | 6 | 2 |
| 911* | 3,4-dimethylheptane | 16 | 2 |
| 911* | 3,4-dimethylheptane | | 2 |
| 912* | 3,5-dimethylheptane | 7 | 2 |

TABLE 1-continued

Nonane isomers in a hydrogenated PT3 stream and identification by gas chromatography

| Code | Name | Number of alkene (1) | Level branching |
|------|------|----------------------|-----------------|
| 912* | 3,5-dimethylheptane | | 2 |
| 913 | 4,4-dimethylheptane | 3 | 1 |
| 914 | 3-ethylheptane | 8 | 1 |
| 915 | 3-ethylheptane | 7 | 1 |
| 916 | 2,2,3-trimethylhexane | 6 | 3 |
| 917 | 2,2,4-trimethylhexane | 6 | 3 |
| 918 | 2,2,5-trimethylhexane | 4 | 3 |
| 919 | 2,3,3-trimethylhexane | 4 | 3 |
| 920* | 2,3,4-trimethylhexane | 9 | 3 |
| 920* | 2,3,4-trimethylhexane | | 3 |
| 921 | 2,3,5-trimethylhexane | 7 | 3 |
| 922 | 2,4,4-trimethylhexane | 3 | 3 |
| 923 | 3,3,4-trimethylhexane | 5 | 3 |
| 924 | 3-ethyl-2-methylhexane | 10 | 2 |
| 925 | 3-ethyl-3-methylhexane | 4 | 2 |
| 926 | 3-ethyl-4-methylhexane | 8 | 2 |
| 927 | 4-ethyl-2-methylhexane | 6 | 2 |
| 928 | 2-ethyl-2,2-dimethylpentane | 3 | 3 |
| 929 | 2-ethyl-2,3-dimethylpentane | 2 | 3 |
| 930 | 2-ethyl-2,4-dimethylpentane | 4 | 3 |

*stereoisomers
(1): number of alkene with this backbone structure

From the complete study for the reaction cascade from the olefin oligomer up to the vinyl ester derived from; the inventors have found that ratio of (BR1+BR2)/BR3=Y will determine the throughput of vinylation reaction. When an olefin mixture is used for the Koch reaction wherein Y is above 20 (Ya) the subsequent vinylation reaction is faster than when an olefin mixture is used wherein Y is below 20 (Yb).

It is hypothesized that a Ya type PT3 after the Koch reaction using mild reaction conditions (80° C., 80 bar of CO and about 18% weight water in the acid catalyst) leads to a composition of branched carboxylic acids derived from the branching level of the Ya-PT3 composition without significant isomerisation during the reaction and lead to an acid isomeric composition with a higher proportion of "non blocking" isomers (NB), as defined below, over the amount of "blocking" isomers (B).

Blocking Isomers of Neo-Caboxylic Acids

Whereas the carbon atom in alpha position of the carboxylic acid is always a quartenary carbon atom, the carbon atom(s) in β position can either be secondary, tertiary, or quaternary. Neodecanoic acids (V10) with a tertiary or a quaternary carbon atom in the β position are defined as blocking isomers (Schemes a & b).

Scheme a: Example of a Non-blocked V10 Structure

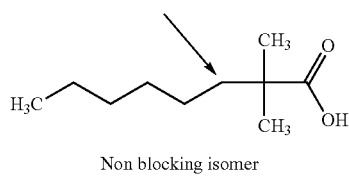

Non blocking isomer

Scheme b: Example of a Blocked V10 Structure β

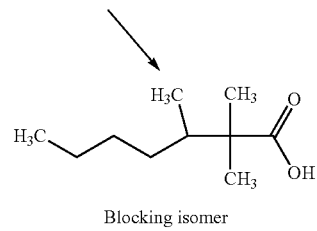

Blocking isomer

Blocking isomers not only comprise alkyl groups on the (alpha) carbon next to the acid group, which is therefore a quaternary carbon atom, but also one or more alkyl groups attached to the next (beta.β) atom. Non-blocking isomers on the other hand have beta atoms (β) that are secondary (i.e., without branching).

Preferably, vinylation is carried out on a mixture of carboxylic acids containing both non blocking isomers and blocking isomers in a ratio NB/B that is greater than 1.5.

Interestingly, by selecting more severe reaction conditions for the production of the branched carboxylic acids (by Koch reaction) starting from a type Yb PT3 feed the inventors have found that they could produce Ya-type C10 branched carboxylic acids.

Isomerisation may be performed in the Koch reaction by various means. For instance, the isomerisation seems to take place under the Koch conditions when the level of water in the catalyst is below 12 wt % for a residence time of at least 30 minutes.

By including an isomerisation step in the Koch reaction, resulting in a NB/B ratio of at least 1.5, it was therefore found that the throughput of the reaction improved from a 4.2-4.5 ton/hour for a type Yb PT3 feed to 5.3-5.6 ton/hour.

This improvement was found, starting from the branched carboxylic acids produced according to the modified Koch reaction and reacting the same with acetylene and Zn catalyst.

The invention claimed is:

1. A process for the manufacture of α,α-branched carboxylic acid vinyl esters comprising:
   converting a propylene oligomer olefin feed with CO and water under Koch reaction conditions and wherein the propylene oligomer olefin feed has an isomer ratio of (BR1+BR2)/BR3=Ya above 20, with BR1=weight of propylene oligomer olefin with one branching alkyl group, BR2=weight of propylene oligomer olefin with two branching alkyl groups and BR3=weight of propylene oligomer olefin with three or more branching alkyl groups to make an acid with a ratio of Non Blocking isomers (NB) versus Blocking isomers (B) of NB/B above 1.5, where the α carbon atom is always quaternary, the carbon atom(s) in β position can either be secondary, tertiary, or quaternary, acids with a tertiary or a quaternary carbon atoms in the β position are defined as blocking isomers,
   converting the resulting acids into vinyl esters.

2. The process of claim 1 wherein the propylene olefin feed is mainly a trimer of propylene or mainly a tetramer of propylene.

3. The process of claim 1 wherein the resulting acid is reacted with acetylene in presence of a zinc catalyst.

4. The process of claim 3 wherein the propylene oligomer is mainly a trimer of propylene with Ya composition and wherein the resulting acids are reacted with acetylene in presence of a zinc salt to produce vinyl esters of branched carboxylic acids with a copolymer Tg of 26.5° C. or lower.

5. A copolymer comprising of the vinyl esters produced according to claim 1.

6. A process for the manufacture of $\alpha,\alpha$-branched carboxylic acids comprising:

converting a propylene oligomer olefin feed with CO and water under Koch reaction conditions and wherein the propylene oligomer olefin feed has an isomer ratio of (BR1+BR2)/BR3=Ya above 20, with BR1=weight of propylene oligomer olefin with one branching alkyl group, BR2=weight of propylene oligomer olefin with two branching alkyl groups and BR3=weight of propylene oligomer olefin with three or more branching alkyl groups to make an acid with a ratio of Non Blocking isomers (NB) versus Blocking isomers (B) of NB/B above 1.5, where the $\alpha$ carbon atom is always quaternary, the carbon atom(s) in $\beta$ position can either be secondary, tertiary, or quaternary, acids with a tertiary or a quaternary carbon atoms in the $\beta$ position are defined as blocking isomers.

7. The process of any one of claim 1, wherein the resulting acid is reacted with acetylene in presence of a zinc catalyst with a throughput of the reaction of at least 5.3 ton/hour.

* * * * *